(12) United States Patent
Appelqvist et al.

(10) Patent No.: US 7,192,572 B2
(45) Date of Patent: Mar. 20, 2007

(54) COMPOUND DELIVERY SYSTEMS

(75) Inventors: Ingrid Anne Marie Appelqvist, Vlaardingen (NL); Mark Emmett Malone, Bedford (GB); Asish Nandi, Bedford (GB)

(73) Assignee: Conopco, Inc., Edgewater, NJ (US)

( * ) Notice: Subject to any disclaimer, the term of this patent is extended or adjusted under 35 U.S.C. 154(b) by 314 days.

(21) Appl. No.: 10/740,252

(22) Filed: Dec. 18, 2003

(65) Prior Publication Data

US 2004/0151674 A1 Aug. 5, 2004

(30) Foreign Application Priority Data

Dec. 20, 2002 (GB) ................... 0229811.5

(51) Int. Cl.
*A61Q 11/00* (2006.01)
*A61K 8/00* (2006.01)
*A61K 31/505* (2006.01)
*C07D 239/02* (2006.01)

(52) U.S. Cl. ............... 424/49; 424/54; 424/401; 424/439; 426/66; 426/585; 514/345; 514/269; 514/901; 514/938; 544/315; 544/316; 544/318

(58) Field of Classification Search ............... None
See application file for complete search history.

(56) References Cited

U.S. PATENT DOCUMENTS

| | | | |
|---|---|---|---|
| 3,821,221 A | 6/1974 | Podesva et al. | |
| 4,835,002 A | 5/1989 | Wolf et al. | |
| 4,971,788 A * | 11/1990 | Tabibi et al. | ............ 424/49 |
| 5,045,337 A | 9/1991 | El-Nokaly et al. | |
| 5,283,056 A | 2/1994 | Chung et al. | |
| 5,405,604 A * | 4/1995 | Hall | ............ 424/54 |
| 5,416,075 A * | 5/1995 | Carson et al. | ............ 514/23 |
| 2003/0207851 A1* | 11/2003 | Wei | ............ 514/171 |
| 2004/0067970 A1* | 4/2004 | Foster et al. | ............ 514/269 |

FOREIGN PATENT DOCUMENTS

| | | |
|---|---|---|
| AU | 58449/98 | 9/1998 |
| EP | 1 121 927 | 8/2001 |
| EP | 1 122 233 | 8/2001 |
| EP | 0 829 206 | 12/2002 |
| WO | 99/62357 | 12/1999 |
| WO | WO 99/62357 | * 12/1999 |
| WO | 01/21146 | 3/2001 |
| WO | 02/102327 | 12/2002 |

OTHER PUBLICATIONS

Charrois et al. Pediatrics in Review, 2006, 27, (abstract) see Definition and Description.*
Kale, N.J. et al., "Studies on microemulsions using Brij 96 as surfactant component and glycerin, ethylene glycol and propylene glycol as co-surfactant components", *Int'l. J. of Pharmaceutics*, 57, pp. 87-93, (1989).
Stamatis, H., Xenakis, A., Menge U. Kolisis F.N.: "Kinetic Study of Lipase Catalyzed Esterification Reactions in Water-in-Oil Microemulsions", Biotechnology and Bioengineering, vol. 42, No. 8, 1993, pp. 931-937, XP002276789, materials and methods.

* cited by examiner

*Primary Examiner*—Frederick Krass
*Assistant Examiner*—Lezah Roberts
(74) *Attorney, Agent, or Firm*—Michael P. Aronson

(57) ABSTRACT

A composition comprising
(a) from 0.005% to 0.5% by weight of a cooling compound;
(b) from 0.1% to 10% by weight of an emulsifiable substance;
(c) from 0.15% to 15% by weight of a surfactant;
(d) optionally up to 5% by weight, preferably from 0.05% to 5% by weight of a cosurfactant.

3 Claims, No Drawings

COMPOUND DELIVERY SYSTEMS

FIELD OF THE INVENTION

The invention relates to delivery systems for compounds which are capable of producing a cooling sensation when they are brought into contact with the human body. Such compounds have applications in many fields, particularly in oral and personal hygiene product, foodstuffs and beverages.

BACKGROUND OF THE INVENTION

Tetrahydropyrimidine-2-one compounds are known to be useful in pharmaceutical preparations. For example, U.S. Pat. No. 3,821,221 discloses a number of such compounds, and their effect as central nervous system stimulants or depressants. The compounds are said to be of value for therapeutic applications as potential psychotropic drugs.

As a result of pharmacological research into these tetrahydropyrimidine-2-one derivatives, it was discovered that icilin (also known as AG-3-5, chemical name 1-[2-hydroxyphenyl]-4-[2-nitrophenyl]-1,2,3,6-tetrahydropyrimidine-2-one) produced sensations of coldness when in contact with mucous membranes (nostrils, lips and eyelids) of the researchers, and also when ingested (see Wei et al, *J. Pharm. Pharmacol.* 1983, 35:110–112).

A known compound for producing a sensation of cold is menthol (2-isopropyl-5-methyl-cyclohexanol), which has been extensively applied as an additive in, for example, foodstuffs and oral hygiene products. It is used primarily because it elicits a sensation of coolness in the mouth, and because it has a pleasing mint flavour and odour. The cooling effect of menthol is due to the action of menthol on the nerve endings of the human body which detect hot and cold stimuli. In particular, menthol is believed to activate cold receptors on nerve endings. However, the use of menthol is limited by its strong minty smell and relative volatility.

It was found that icilin was capable of producing the same cooling effect as menthol. Icilin has a number of advantages over menthol, for example it is more potent, and has a lower acute toxicity, due to its lack of anaesthetic properties. Icilin was considered to be a particularly useful compound for pharmacological applications because it lacks the flavour and odour of menthol and is not readily absorbed through the skin. However, icilin has not been disclosed as a replacement for menthol for non-pharmaceutical applications.

It has now been found that to formulate cooling compounds in the form of microemulsions to be incorporated in food products or beverage produces a lingering cooling effect and sometimes also, a smooth mouthfeel. "Mouthfeel" is used herein to describe the mingled experience derived from the sensations of the oral cavity during consumption of a food or beverage. It involves a product's entire physical and chemical interaction in the mouth relating to the density, viscosity, surface tension, mouthcoating, astringency, smoothness, lubricity and such like.

U.S. Pat. No. 4,835,002 describes microemulsions of essential oils which also contain certain alcohols, surfactant components and water and which are used in foods and beverages.

U.S. Pat. No. 5,045,337 describes edible water-in-oil microemulsions which are thermodynamically stable, clear and homogeneous and which contain a polar solvent, a specific polyglycerol mono diester and a lipid which may be a longer chain triglyceride.

U.S. Pat. No. 5,283,056 describes stable transparent oil-in-water microemulsion concentrates containing water, one or more hydrophobic flavour or fragrance oils and one or more surfactant components.

Australian Patent Application 58449/98 describes oil-in-water microemulsions contain triglycerol monofatty acid esters as emulsifier and a lipophilic substance which is a carotenoid, vitamin or polyunsaturated fatty acid as the internal phase of the microemulsion.

International Patent Application 99/62357 describes water-in-oil microemulsions containing flavour precursors which are activated during consumption to provide the flavour to the consumer.

European Patent Application 829206 describes edible microemulsions which contain an oil which may be a medium chain triglyceride comprising C6 to C18 fatty acids which are used to coat foodstuffs so that they brown and crisp when subjected to microwave radiation.

It is also known to make microemulsions using non-food grade oils. A method for 5 making such microemulsions is described in an article by Neelima J. Kale and Loyd V. Allen, Jr., International Journal of Pharmaceutics, 57 (1989) 87–93 entitled "Studies on microemulsions using Brij 96 as surfactant component and glycerin, ethylene glycol and propylene glycol as co-surfactant components". This product contains light mineral oil (i.e. paraffin) which is not suitable for use in foods.

DEFINITION OF THE INVENTION

The present invention is concerned with microemulsions.

A "precursor" to a microemulsion is a mixture of all the components which are needed to make the microemulsion with the exception of the continuous phase. "Medium chained triglyceride" for the purposes of this invention means naturally occurring esters of glycerol with C4 to C14 fatty acids. The medium chain triglyceride has three fatty acid carbon chains each containing 4–14 carbon atoms. The fatty acids may be the same or different. A suitable medium chain triglyceride for use in the present invention may be obtained from coconut oil and is supplied by Quest International under the trade designation MCT OIL KQ 60/40 which contains up to 2% C6 fatty acid, 50–65% C8 fatty acid, 30–45% C10 fatty acid, up to 3% C12 fatty acid and up to 1% C14 fatty acid.

The microemulsion products of the present invention may be incorporated into products, for example food, beverage, oral care product or other products, in several ways:

1) the microemulsion may be prepared from its components and the continuous phase and the resultant microemulsion can then be added to any remaining components;
2) the components of a microemulsion precursor may be mixed with each other and added to the continuous phase to make the microemulsion in situ which is then admixed with any remaining components of the product; or
3) the components of a microemulsion precursor may be mixed with the continuous phase to prepare a concentrated microemulsion in situ and this may then be diluted admixing with any remaining components of the product.

Variations of these various processes are also possible. For example, in cases (2) or (3), some or all of any remaining components may be pre-incorporated in the continuous phase. In cases (1) and (2), some of the microemulsion components may be incorporated with the remaining components (if any), in which case a microemulsion as such may not form until that stage.

In the broadest sense, and in a first aspect, the present invention may be considered to reside in a microemulsion premix which comprises
(a) from 0.005% to 0.5% by weight of a cooling compound;
(b) from 0.1% to 10% by weight of an emulsifiable substance;
(c) from 0.15% to 15% by weight of a surfactant;
(d) optionally up to 5% by weight, preferably from 0.06% to 5% by weight of a cosurfactant.

A microemulsion product according to a second aspect of the invention may therefore comprise a composition according to the first aspect of the invention dispersed in a continuous phase, whether the composition according to the first aspect of the invention was incorporated as such into the product or whether its components were introduced in any other way.

A microemulsion according to the second aspect of the present invention may typically comprise from 0.45% to 30% by weight of the total components of the first aspect of the invention.

When the emulsifiable substance comprises water and the continuous phase comprises oil, then the micoemulsion will be a water-in-oil microemulsion, suitable for product forms such as spreads, dressings and ice creams.

When the emulsifiable substance comprises an oil and the continuous phase comprises water, then the microemulsion will be an oil-in-water microemulsion, suitable for product forms such as beverages, water ices, toothpaste and mouthwashes.

Another aspect of the present invention relates to a microemulsion or precursor thereto for altering the flavour release of a cooling compound and/or for improving the mouthfeel of a product containing a cooling compound, the microemulsion comprising from 0.0025% to 0.5% by weight of the cooling compound, from 0.1% to 10% by weight of an oil that comprises one or more medium chain triglycerides; from 0.15% to 15% by weight of a surfactant component and optionally, from 0.05% to 5% by weight of co-surfactant component.

A preferred microemulsion or precursor thereto for altering the release profile of a cooling compound comprises from 0.0025% to 0.1% by weight of the cooling compound; from 0.12% to 0.4% by weight of an oil component that comprises one or more medium chain triglycerides; 0.23% to 0.45% by weight of a surfactant component and optionally 0.07% to 0.15% by weight of co-surfactant component.

A preferred microemulsion or precursor thereto for improving the mouthfeel of a cooling compound comprises from 0.0001% to 0.1% by weight of the cooling compound, from 0.12% to 0.4% by weight of an oil component that comprises one or more medium chain triglycerides; 0.23% to 0.45% by weight of a surfactant component and optionally 0.07% to 0.15% by weight of co-surfactant component.

The present invention also relates to a food or beverage product comprising an oil-in-water microemulsion which comprises water from 0.0001% to 0.05% by weight of a cooling compound, from 0.1% to 10% by weight of an oil component that comprises one or more medium chain triglycerides from 0.15% to 15% by weight of a surfactant component, and optionally from 0.05% to 5% by weight of co-surfactant component the balance of the beverage product being water and one or more other component, based on the weight of the product.

The present invention further provides an oral care product comprising an oil-in-water microemulsion which comprises water from 0.005% to 0.15% by weight of a cooling compound, from 0.1% to 10% by weight of an oil component that comprises one or more medium chain triglycerides from 0.15% to 15% by weight of a surfactant component, and optionally from 0.05% to 5% by weight of co-surfactant component the balance of the oral care product being water and one or more other components, based on the weight of the product.

Suitable other components of an oral care product include thickening agents, binders, humectants, surfactants and abrasives.

The present invention also relates to a spread or dairy-based product which comprises a water-in-oil emulsion which comprises an oil compound, from 0.0001% to 0.05% by weight of a cooling compound, from 0.001% to 2.5% by weight of water, from 0.001% to 2.5% by weight of a surfactant component and optionally from 0.0001% to 0.15% by weight of co-surfactant.

DETAILED DESCRIPTION OF THE INVENTION

The present invention concerns microemulsions for altering the release profile of a cooling compound. The microemulsion is an oil-in-water emulsion that contains a cooling compound, an oil component that comprises one or more medium chain triglycerides, a surfactant component, an optional co-surfactant component; and water. Every component must be suitable for use in a food or beverage product in question.

The Cooling Compound

The microemulsion of the present invention may comprise a single cooling compound or two or more different cooling compounds. As used herein, reference to "a cooling compound" includes all such possibilities.

One preferred cooling compound is menthol. Another preferred class of cooling compounds comprises those of formula (I):

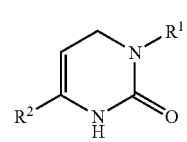

[I]

wherein $R^1$ and $R^2$ are independently selected from hydrogen or halogen atoms; hydroxy, cyano, nitro, mercapto, carbonyl, sulfone and carboxy groups; or optionally substituted alkyl, alkenyl, alkoxy, alkylthio, aryl, aryloxy, arylthio, amino, siloxy, ester and heterocyclic groups.

A preferred sub-class of cooling compounds comprises those of formula (II):

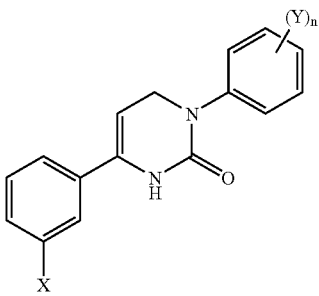

[II]

or a salt thereof, wherein X is a hydrogen or halogen atom, or an alkyl or alkoxy group; Y is hydroxy or alkoxy; and n is 0, 1, 2 or 3.

Unless otherwise specified in the following description, alkyl represents a linear or cyclic saturated hydrocarbon which may be straight-chain or branched, and preferably contains up to 20 carbon atoms. Similarly, alkenyl represents a linear or cyclic, straight-chain or branched unsaturated hydrocarbon which preferably contains up to 20 carbon atoms. When an alkyl group is linear, it preferably contains from 1 to 10, more preferably from 1 to 6 carbon atoms. Suitable examples include methyl, ethyl, propyl, butyl, pentyl and hexyl, and isomers thereof. For example, a $C_4$ group can be present in the form of n-butyl, iso-butyl, sec-butyl or tert-butyl. When an alkyl group is cyclic, it preferably contains from 5 to 10 carbon atoms, and may be, for example, cyclopentyl, cyclohexyl, cycloheptyl, decalin or adamantyl.

Alkoxy and alkylthio represent alkyl groups linked by an oxygen atom or a sulphur atom respectively, with the alkyl portion being as defined above.

Aryl represents a hydrocarbon comprising at least one aromatic ring, and may contain from 5 to 18, preferably from 6 to 14, more preferably from 6 to 10, and most preferably 6 carbon atoms. Typical aryl groups include phenyl, naphthyl, phenanthryl, anthracyl, indenyl, azulenyl, biphenylenyl, and fluorenyl groups. Particularly preferred aryl groups include phenyl, naphthyl and fluorenyl, with phenyl being most preferable.

Aryloxy and arylthio represent aryl groups linked by an oxygen atom or a sulphur atom respectively, with the aryl portion being as defined above.

Amino represents a group having the general formula —NR'R" where R' and R" are independently selected from hydrogen atoms and alkyl groups. When R' and R" are alkyl groups they preferably contain from 1 to 10, more preferably from 1 to 4, carbon atoms. Possible amino groups include —NH$_2$, methyl amino (i.e. —NHMe), ethyl amino, propyl amino, butyl amino, sec-butyl amino, tert-butyl amino, pentyl amino, hexyl amino, heptyl amino, octyl amino, stearyl amino, dimethyl amino (i.e. —NMe$_2$), diethyl amino, dipropyl amino, dibutyl amino, disec-butyl amino, ditert-butyl amino, dipentyl amino, dihexyl amino, diheptyl amino, dioctyl amino and distearyl amino. Mixed dialkyl amino groups (i.e. where R' and R" are different) are also possible.

Siloxy represents a group of general formula —OSiR$_3$, where each R group is independently selected from the group consisting of a hydrogen atom and an alkyl group. The alkyl group preferably has from 1 to 6, more preferably 1 to 4, carbon atoms The term ester (also known as alkoxycarbonyl) represents a group of formula —C(O)OR where R is a hydrogen atom or an alkyl group. Preferably the alkyl group has from 1 to 6, more preferably from 1 to 4, carbon atoms.

The term heterocyclic represents groups having between 3 and 20, more preferably between 3 and 10, carbon atoms and having one or more 4, 5, 6 or 7 member saturated or unsaturated rings containing 1, 2 or 3 oxygen, nitrogen or sulphur atoms. Heterocyclic groups containing saturated rings include groups based on pyrrolidine, piperidine, tetrahydro-thiophene, dithiolane, oxathiolane, oxazolidine, oxazinane, oxathiane, tetrahydro-thiopyran, tetrahydro-pyran, dioxolane, dioxane, thiazinane, dithiane, thiazolidine, imidazolidine, hexahydro-pyrimidine and tetrahydro-furan.

Heterocyclic groups containing aromatic rings (heteroaryl groups) include thienyl, benzothienyl, naphthothienyl, thianthrenyl, furyl, pyranyl, isobenzofuranyl, chromenyl, xanthenyl, phenoxathinyl, pyrrolyl, imidazolyl, pyrazolyl, pyridyl, pyrazinyl, pyrimidinyl, pyridazinyl, indolizinyl, isoindolyl, indolyl, indazolyl, purinyl, quinolizinyl, isoquinolyl, quinolyl, phthalazinyl, naphthyridinyl, quinazolinyl, cinnolinyl, pteridinyl, carbazolyl, carbonlinyl, phenanthridinyl, acridinyl, perimidinyl, phenanthrolinyl, phenazinyl, isothiazolyl, phenothiazinyl, isoxazolyl, furazanyl, quinoxalynyl, quinazolynyl, pylazinyl, acrydinyl, phenadinyl, furluryl, isochiazolyl, isoquixazolyl, phenoquisadinyl, benzthiazolyl, benzoxazylyl, benzoinidazolyl, pyranthrenyl, oparenyl and phenoxazinyl.

The term halogen represents any halogen atom selected from fluorine, chlorine, bromine and iodine, with fluorine and chlorine being preferred.

Where any of the groups defined above are described as being optionally substituted, the substituent groups may include halogen atoms, hydroxy, thiol, cyano, amino, silyl, nitro, alkyl, haloalkyl, cycloalkyloxy, alkoxy, haloalkoxy, alkoxycarbonyl, carboxyl, carbonyl, alkanoyl, alkylthio, alkylsulphinyl, sulphinyl, alkylsulphonyl, sulphonato, alkylsulphonato, aryl, arylalkyl, alkaryl, aryloxy, arylsulphinyl, arylsulphonyl, arylsulphonato, sulphonamide, carbamoyl, carbamido, alkylamido, alkenyl, alkenyloxy and alkynyl, as well as heterocyclic groups. The preferred optional substituents are halogen atoms, and nitro, hydroxy, alkyl, haloalkyl, alkoxy and carboxy groups. When the optional substituent is an alkyl, haloalkyl or alkoxy group, the alkyl portion of the substituent preferably contains from 1 to 6 carbon atoms, and is preferably linear. Particularly preferred optional substituents are chlorine atoms, and nitro, hydroxy, methyl, ethyl, tertiary butyl and methoxy groups.

The cooling compound(s) have the ability to produce a cooling sensation when in contact with the skin and/or mucosal membrane of a human or animal body. A "cooling sensation" as used throughout is thus intended to mean any sensation of coolness which is perceived by human or animal body. Such a cooling sensation is analogous to the sensation produced by compounds such as menthol, and/or the sensation elicited when cold-sensitive receptors, such as those identified in McKemy et al, Nature, Vol. 416, 2002, 52–58, are stimulated.

In the compounds of formula (I), it has been found that preferred $R^1$ groups include optionally substituted alkyl or aryl groups. The alkyl group can be a linear group such as a $C_{1-10}$ aliphatic chain, or a cyclic group, such as a $C_{3-10}$ cyclic hydrocarbon. It is preferred that $R^1$ is an optionally substituted aryl or cyclic hydrocarbon group, such as a phenyl or cyclohexyl group.

The preferred $R^2$ groups include hydrogen atoms, or optionally substituted alkyl or aryl groups. Again, the $R^2$ group can be a linear, aliphatic chain, or a cyclic hydrocarbon, as for $R^1$. The preferred groups are optionally substituted aryl and cyclic hydrocarbon groups, with phenyl and cyclohexyl being particularly favoured. Alternatively, it may be desirable to replace these cyclic groups with other groups, such as a hydrogen atom, a straight chain alkyl group (e.g. a $C_{1-10}$ alkyl group) or a branched chain alkyl group (e.g. a tertiary butyl group).

A number of compounds have been synthesised, and show an ability to elicit a cooling sensation. Preferred compounds include 1-(2'-methoxyphenyl)-4-(3"-nitrophenyl)-1,2,3,6-tetrahydropyrimidine-2-one, 1-phenyl-4-(3"-nitrophenyl)-1,2,3,6-tetrahydropyrimidine-2-one, 1-(2'-methoxyphenyl)-4-(3"-chlorophenyl)-1,2,3,6-tetrahydropyrimidine-2-one, 1-phenyl-4-(3"-chlorophenyl)-1,2,3,6-tetrahydropyrimidine-2-one, 1-(2'-methylphenyl)-4-(3"-nitrophenyl)-1,2,3,6-tetrahydropyrimidine-2-one, 1-(2'-methoxyphenyl-4-(3"-methoxyphenyl)-1,2,3,6-tetrahydropyrimidine-2-one or 1-phenyl4-(3"-methoxyphenyl)-1,2,3,6-tetrahydropyrimidine-2-one to produce a cooling sensation.

The compounds may be used alone, or in a composition in combination with another substance or substances such as a carrier. The nature of these additional substances, and the relative proportions of components of the composition will depend on a number of factors, such as the specific use for which the composition is employed. The compositions may be used in a variety of applications, such as those discussed above.

The compounds of formula (I) can be made according to a general process shown in Scheme 1:

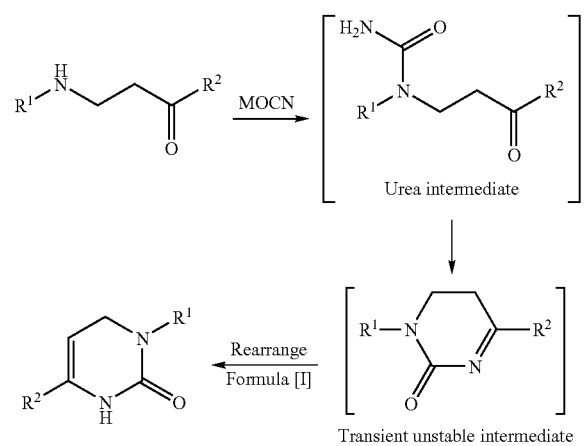

The β-amino-ketone compound required in Scheme 1 can be made by any suitable process, for example according to the synthetic route described in Examples 1 and 2 below, or via the synthetic routes disclosed in the examples of U.S. Pat. No. 3,821,221.

Preferred embodiments of the invention will now be described by way of example only. Further modification within the scope of the present invention will be apparent to the person skilled in the art.

The Oil Component

The oil component of the microemulsion must contain one or more medium chain triglycerides. Such triglycerides can be obtained from naturally occurring oils such as coconut or palm kernel oil and may be fractionated to give triglycerides containing only the desired fatty acid compositions. The fatty acid components of the medium chain triglycerides utilised in the present invention contain 4 to 14 carbon atoms. The fatty acids constituting the triglyceride may be the same or different. Triglycerides in which the fatty acids contain more than 12 carbon atoms (for example triglycerides obtained from sunflower oil which have mainly C18 fatty acids) are not suitable for use on their own in the present invention. However if triglycerides having C4 to C8 fatty acids are present, triglycerides having fatty acids with more than twelve carbon atoms may be incorporated into the microemulsions of the present invention.

The Surfactant Component

The surfactant component may comprise one or more surface active agents or amphophile which lowers the surface and interfacial tension. Oil in water microemulsions are better formed with surfactant components within the hydrophilic lipophilic balance (HLB) values of 8–18. Non-ionic surfactants are preferably used as they are less toxic and not influenced by electrolytes or pH. Polyethylene glycol oleyl ethers (for example those available under the trade name Brij 96 manufactured by Fluka and supplied by Sigma Aldrich) are especially preferred. The chemical structure of Brij 96 is

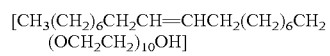

Other suitable surfactants include nonionic surfactants having HLB values in the range of 8–18. Such surfactants may include lecithins, polyglycerol esters, polyoxyethylene sorbitates, polyoxyethylene esters of fatty acids, polyethylene glycols, propylene glycols etc.

The Co-Surfactant

The co-surfactant component (which is optional in some aspects of the invention) may be purified glycerol. Suitable food grade glycerol may be that supplied by Pricene or may be glycerol obtained from from vegetable sources (for example Glycerine 4810 supplied by Fina Chemicals). Other suitable cosurfactant components that may be used to form the microemulsions of the present invention are variants having the same functionalities as glycerol, for example erythritol or short chain alcohols such as butanol, pentanol, hexanol or heptanol.

Processing

The microemulsion precursors of the present invention may be prepared by mixing the components of the precursor in a suitable manner, for example mixing the surfactant component [for example polyethylene glycol oleyl ethers (Brij 96)] and the cosurfactant component (for example glycerol) at the desired ratios using a magnetic stirrer at temperatures above 60° C. The desired amount of the medium chain triglycerides oil and the cooling compound may then be added and the mixture mixed thoroughly. The cooling compound is preferably solubilised in the oil by heating to 80° C. or more. The microemulsions of the present invention may then be made by adding hot water (>60° C.) to this mixture of the microemulsion precursors.

Product Forms

Preferred product forms containing a microemulsion according to the present invention include foods, beverages and oral care products.

(a) Foods

Suitable food products which may incorporate a microemulsion according to the present invention include spreads, mayonnaise, sauces, savoury products and ready-heat meals (all of the latter preferably incorporating the microemulsion as a water emulsion). Others include ice confections such as ice cream (including yoghurt ice cream) water ices and confectionery items.

(b) Beverages

Typical beverages both carbonated and non-carbonated, and/or alcoholic and non-alcoholic beverages. Some typical examples are tea based products, fruit juice based drinks and fruit squashes, energy drinks, falvoured milk shakes and milk and yoghurt-based drinks in general.

"Tea beverages" as used herein describes beverages made by infusing plant leaf material or beverages made from concentrates that have been derived from the plant leaf material. The leaf material may advantageously be derived from Camellia sinensis var. sinensis or Camellia sinensis var. assamica and may be unfermented (green tea), partially fermented (Oolong) or fermented (black tea). Other sources of leaf material may however be used in the practice of the present invention. These include rooibos tea obtained from Aspalathus linearis, herbal teas (for example camomile, rosehip, fennel, nettle, peppermint or lemon verbena). It is also intended to include leaf material produced by blending two or more of any of these leaf materials. "Leaf tea" for the purposes of this invention means a tea product that contains one or more tea origins in an uninfused form. Leaf tea includes green tea, black tea and oolong tea or the leaf material from other plants which may be used to prepare tea beverages. Beverages derived from Camellia sinensis are preferred and are hereafter referred to as "tea-based beverages".

(c) Oral Care Products

Preferred oral care products are toothpaste and mouthwashes.

The present invention will now be described with reference to the following non-limiting examples.

EXAMPLE 1

Typical formulation for a fruit flavoured tea beverage

| Ingredient | % w/w |
|---|---|
| Sugar | 7.2 |
| Tea powder | 0.14 |
| Acids & salts | 0.215 |
| Fruit juice & flavour | 0.38 |
| Brij 96 | 0.15 |
| Glycerol | 0.05 |
| Medium Chain Triglycerides | 0.1 |
| Cooling Active | 0.005 |
| Water | balance |

EXAMPLE 2

Typical formulation for Water ices

| Ingredient | % w/w |
|---|---|
| Sugars | 20.63 |
| Citric Acid | 0.45 |
| Flavour | 0.015 |
| Brij 96 | 0.3 |
| Glycerol | 0.1 |
| Medium Chain Triglycerides | 0.2 |

-continued

Typical formulation for Water ices

| Ingredient | % w/w |
|---|---|
| Cooling Active | 0.01 |
| Water | balance |

EXAMPLE 3

Typical formulation for toothpaste

| Ingredient | % w/w |
|---|---|
| Abrasive & Thickening silica | 18.0 |
| Sorbitol & Polyethylene glycol | 50.0 |
| Sodium Lauryl Sulphate | 1.5 |
| Cellulose gum | 0.9 |
| Sodium Fluoride | 0.32 |
| Sweeteners & other minors | 1.17 |
| Peppermint flavour | 1.0 |
| Brij 96 | 3.0 |
| Glycerol | 1.0 |
| Medium Chain Triglycerides | 0.5 |
| Cooling Active | 0.05 |
| Water | balance |

It was found that using as cooling active, respectively menthol or 1-(2'-methoxyphenyl)-4-(3"-nitrophenyl)-1,2,3,6-tetrahydropyrimidine-2-one, ingestion in the form of the compositions of the above examples prolonged the cooling effect perceived, relative to the same amount of the cooling active alone.

The invention claimed is:

1. An oil in water microemulsion comprising from 0.45% to 30% by weight of a composition comprising:
   a) from 0.005% to 0.5% by weight of a cooling compound having formula (I);

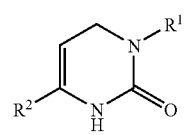

[I]

wherein $R^1$ is 2-methoxyphenyl and $R^2$ is 3-nitrophenyl;
   b) from 0.1% to 10% by weight of an emulsifiable substance comprising a medium chain triglyceride;
   c) from 0.15% to 15% by weight of a surfactant selected from the group consisting of polyethylene glycol oleyl ethers, lecithins, polyglycerol esters, polyoxyethylene sorbates, polyoxyethylene esters of fatty acids, polyethylene glycols, propylene glycols and mixtures thereof;
   d) optionally up to 5% by weight of a cosurfactant.

2. The microemulsion of claim 1 in the form of a beverage, water ice, toothpaste or mouthwash.

3. The microemulsion of claim 1 wherein the cosurfactant is glycerol, erythritol or a short chain alcohol.

* * * * *